United States Patent [19]

Boone et al.

[11] Patent Number: 5,104,651

[45] Date of Patent: Apr. 14, 1992

[54] STABILIZED HYDROPHOBIC PROTEIN FORMULATIONS OF G-CSF

[75] Inventors: Thomas C. Boone, Newbury Park; William C. Kenney, Thousand Oaks, both of Calif.

[73] Assignee: Amgen Inc., Thousand Oaks, Calif.

[21] Appl. No.: 285,159

[22] Filed: Dec. 16, 1988

[51] Int. Cl.$^5$ .............................................. A61R 37/02
[52] U.S. Cl. ..................................... 424/85.1; 514/2; 514/8; 514/12; 514/21; 514/970; 530/351; 435/69.5; 435/69.52; 435/69.6
[58] Field of Search ............................ 424/85.1, 85.2; 514/2.8, 12, 21, 970; 530/351, 395; 435/69.5, 69.52, 69.6

[56] References Cited

U.S. PATENT DOCUMENTS

| | | | |
|---|---|---|---|
| 4,623,717 | 11/1986 | Fernandes et al. | 530/351 |
| 4,645,830 | 2/1987 | Yasushi et al. | 530/351 |
| 4,647,454 | 3/1987 | Cymbalista | 530/351 |
| 4,675,184 | 6/1987 | Hasegawa et al. | 424/85.7 |
| 4,810,643 | 3/1984 | Souza | 435/91 |
| 4,833,127 | 5/1989 | Oho et al. | 530/351 |
| 4,992,271 | 2/1991 | Fernandes | 530/351 |

OTHER PUBLICATIONS

Wang et al. *J. Parenteral Drug Assoc* 1980, vol. 34, pp. 452–462.

Wang et al., *J. Parenteral Science & Technology*, 1988, vol. 42, pp. 53–526.

*Primary Examiner*—Garnette D. Draper
*Attorney, Agent, or Firm*—Henry P. Nowak; Richard J. Mazza; Daniel M. Chambers

[57] ABSTRACT

A stable pharmaceutically acceptable formulation containing a pharmaceutically acceptable amount of a protein is disclosed. Also disclosed are associated means and methods for preparing such formulations.

22 Claims, 2 Drawing Sheets

| | | | | | | | | |
|---|---|---|---|---|---|---|---|---|
| A | B | C | D | E | F | G | H | I |

STABILIZED HYDROPHOBIC PROTEIN FORMULATIONS OF G-CSF

FIELD OF THE INVENTION

The present invention is directed to pharmaceutical formulations containing a protein and to methods for making and using such formulations. More particularly, this invention relates to such pharmaceutical formulations having increased stability. The formulations are also very stable during processing. Formulations are provided for immediate, safe, effective therapeutic administration to human subjects.

BACKGROUND OF THE INVENTION

Granulocyte Colony Stimulating Factor

Granulocyte Colony Stimulating Factor (G-CSF), in its natural form comprises two forms: a protein having 174 amino acids, and a form having three additional amino acids. Both forms have five cysteine residues; four forming two disulfide bonds, and one free. In its natural form G-CSF is a glycoprotein. G-CSF supports the growth of predominantly neutrophil colonies in a colony-forming (CFU-GM) assay, and in the presence of accessory cells, supports the growth of early erythroid (BFU-E) and pluripotential progenitors (CFU-GEMM) (granulocytes, erythrocytes, monocytes, and macrophages). G-CSF is also capable of promoting the differentiation of some myeloid leukemic cell lines (e.g., HL-60, WEHI-3B-D+), fresh myeloid leukemic cells, and has been reported to enhance the chemotactic peptide binding on peripheral blood neutrophils. In addition, G-CSF can significantly increase the ability of neutrophils to kill tumor targets in vitro through antibody-dependent cellular cytotoxicity (ADCC). In vivo experiments with recombinant human G-CSF in hamsters indicate a specific action on the neutrophil lineage with increases of three to sixfold in peripheral blood neutrophils.

Because of its hydrophobic characteristics, G-CSF is difficult to formulate. Examples of attempts to formulate G-CSF are shown in UK Ptent Application GB 2193631. Detergents, such as Tween-80, have been used to maintain G-CSF in a monomeric form and to minimize particulate formation. G-CSF contains five cysteinyl residues, four of which are involved in intrachain disulfide linkage. The free cysteinyl residue is, in general, inaccessible to modification due to folding of the molecule. At elevated temperatures the molecule "breaths" more rapidly and, on occasion, the cysteinyl residues interacts with each other leading to dimer and multimer formation. This phenomenon is enhanced by the presence of a non-ionic surfactant, e.g., Tween-80 TM (polyoxyethylene sorbitan monooleate).

Interleukin-II

Interleukin II ("IL-2"), a glycoprotein with a molecular weight of approximately 15,000, is a member of a group of proteins, called lymphokines, that control the body's immune response. IL-2 is produced by certain white blood cells, lectin- or antigen-activated T cells, and plays a central role in the body's immune system as a lymphocyte regulating molecule.

IL-2 has been reported to enhance thymocyte mitogenesis, to stimulate long-term in vitro growth of activated T-cell clones, to induce cytotoxic T-cell reactivity, to modulate immunological effects on activated B cells and lymphokine activated cells, to induce plaque-forming cell responses in cultures of nude mouse spleen cells, and to regulate production of gamma interferon. It also augments natural killer cell activity and mediates the recovery of the immune function of lymphocytes in selected immunodeficient states.

In order that materials like G-CSF or IL-2 be provided to health care personnel and patients, these materials must be prepared as pharmaceutical compositions. Such compositions must maintain activity for appropriate periods of time, must be acceptable in their own right for easy and rapid administration to humans, and must be readily manufacturable. In many cases pharmaceutical formulations are provided in frozen or in lyophilized form. In these cases, the compositions must be thawed or reconstituted prior to use. The frozen or lyophilized forms are often used to maintain biochemical integrity and the bioactivity of the medicinal agent contained in the compositions under a wide variety of storage conditions. Such lyophilized preparations are reconstituted prior to use by the addition of suitable pharmaceutically acceptable diluent(s), such as sterile water for injection or sterile physiological saline solution, and the like.

Alternatively, the composition can be provided in liquid form appropriate for immediate use. Desirable is a liquid formulation which maintains its activity in long term storage.

Prior formulations of certain hydrophobic proteins lose activity due to formation of dimer and higher order aggregates (macro range) during long-term storage. Other chemical changes, such as deamidation and oxidation may also occur upon storage.

It is an object of the present invention to prepare stable, aggregate-free formulations containing a hydrophobic protein.

A further object of the invention is to provide hydrophobic protein formulations with enhanced characteristics.

A further object of the invention is to provide hydrophobic protein formulations with higher G-CSF concentrations.

A still further object of the invention is to provide formulations containing proteins wherein no component is derived from animals, e.g., natural albumin, thus avoiding possible contamination of the formulation with impurities.

Other objects, features and characteristics of the present invention will become more apparent upon consideration of the following description and the appended claims.

SUMMARY OF THE INVENTION

Objects of this invention are accomplished by a pharmaceutically acceptable formulation comprising, consisting essentially of, or consisting of a pharmaceutically effective amount of a hydrophobic protein stable at acid pH, and acid, wherein said formulation has an acidic pH, and advantageously a low conductivity, i.e. less than about 1000 μmhos/cm. Advantageously the pH of the formulation is about 2.75-4.0, and in a preferred embodiment no buffer is present. The formulation has a purity level which is pharmaceutically acceptable. The formulation is capable of undergoing processing and storage with substantially no dimer or higher order aggregate formation. The invention also comprises a method of stabilizing a formulation comprising the step of combining the protein with acid, advantageously without the addition of any salt, to make a pharmaceutically acceptable formulation having an acidic pH and advantageously an ionic strength of less than 1000 μmhos/cm. Optionally, a tonicity modifier is added.

DETAILED DESCRIPTION OF THE INVENTION

Figure 1:
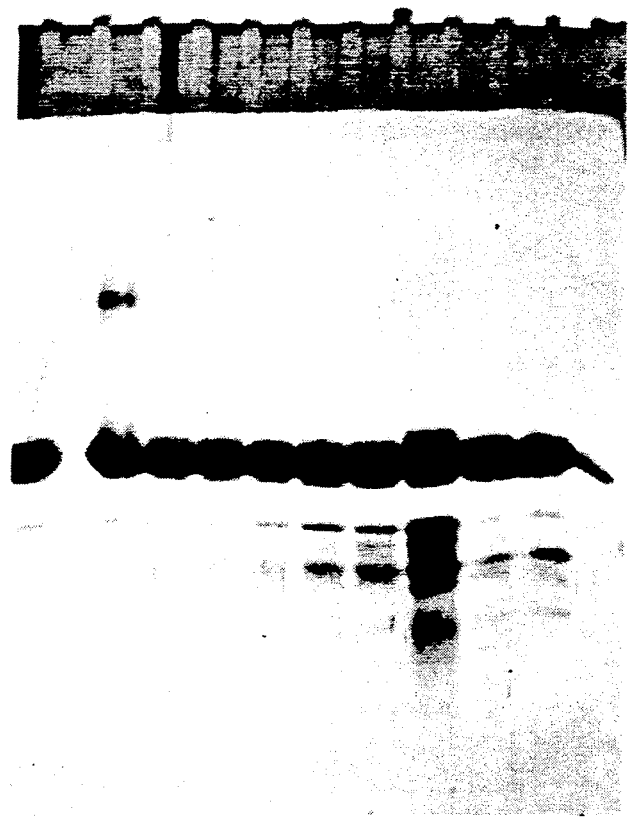
FIG. 1 shows G-CSF prepared at various pH values and run on a 15% gel after reduction of thiol groups.

The present invention is based upon the discovery that at acidic pH values a specific pharmaceutically acceptable formulation of a protein maintains the activity of the protein, and inhibits undesirable reactions that the protein undergoes during processing, reconstitution, and storage. As used herein, the term "processing" includes filtration and filling into vials. The invention is thus directed to such formulations, and to all associated formulations and to means for effectively stabilizing such proteins.

As used herein, the term "hydrophobic proteins stable at acidic pH" denotes proteins produced, for example, from natural source extraction and purification, or by recombinant cell culture systems. The term includes biologically active granulocyte colony stimulating factor (G-CSF), Interleukin-II (IL-2), and other hydrophobic proteins stable at acidic pH, and their equivalents; e.g., differing in one or more amino acid(s) in the overall sequence. Further, the term as used in this application is intended to cover substitution, deletion and insertion of amino acid variants, or post translational modifications. Various forms of G-CSF and methods of production are disclosed in WO 8701132 hereby incorporated by reference. Various forms of IL-2 and methods of production are disclosed in WO 8500817 and U.S. Ser. No. 214,998 filed July 5, 1988, both hereby incorporated by reference.

The formulation of the subject invention comprises:
a) a pharmaceutically acceptable amount of a hydrophobic protein stable at acidic pH; and
b) acid, wherein said formulation has an acidic pH, advantageously no buffer, and advantageously a conductivity of less than 1000 μmhos/cm.

In a preferred embodiment relating to G-CSF, the G-CSF formulation of the subject invention comprises:
a) G-CSF at up to 2 mg/ml; and
b) hydrochloric acid; and
c) mannitol as a tonicity modifier, wherein the pH is 3.2-3.3 and the conductivity of the formulation is less than 500 μmhos/cm.

In the composition of the subject invention, high concentrations of G-CSF (e.g. 1-5 mg/ml) are achievable. The subject formulation eliminates the need for Tween-80. A low conductivity is very advantageous in the subject invention. The pH of the subject formulation is advantageously low.

In general, the formulations of the subject invention may contain other components in amounts preferably not detracting from the preparation of stable forms and in amounts suitable for effective, safe pharmaceutical administration.

Suitable pH ranges for the preparation of the formulations hereof are from about 2.75 to about 4, advantageously about 3.0 to about 3.7, most advantageously 3.2 to 3.3. The formulation pH advantageously should be less than 4 to reduce aggregate formation. pH values are advantageously above 2.75 since values below 2.75 result in substantial peptide bond cleavage. If necessary, the pH is adjusted with acid such as dilute hydrochloric, nitric, phosphoric, or sulfuric acid solutions. In one embodiment, the total acid content is low, i.e. less than about 5 mM to keep the conductivity of the formulation low. In a preferred embodiment no salt (compound derived from an acid by replacing hydrogen with a metal) other than that which is a trace residual by-product of the purification process, is present in the formulation (this embodiment is referred to herein as having no salt).

In a preferred embodiment, no buffer is present other than the protein of interest itself and trace residual by-product of the purification process (this embodiment is referred to herein as having no buffer). The preferred buffer when a buffer is used, is a carboxylic acid buffer. Alternatively, citric, lactic or tartaric acid buffer is used at about 1 mM. A buffer concentration greater than or equal to 0 and less than 2 mM is preferred, most advantageously 1 mM. The buffer concentration is kept low to keep the conductivity of the formulation low. In this concentration range of buffer, minimal aggregation occurs.

The conductivity of the formulations of the subject invention should be less than 1000 μmhos/cm., although at pH values between about 2.75 and 3 the formulation conductivity is optionally higher. Advantageously the conductivity is less than 700 μmhos/cm, and most advantageously less than 500 μmhos/cm. In a preferred embodiment the conductivity is less than 200 μmhos/cm. The conductivity is adjusted by methods such as diafiltration.

Advantageously, formulations of the subject invention are isotonic with the blood of the recipient. A formulation containing about 4-6% (w/v), advantageously 5% (w/v), mannitol as a non-ionic tonicity modifier results in isotonic solution suitable for intravenous injection. The tonicity modifier also acts to stabilize the formulation. As an alternative to mannitol, other sugars or sugar alcohols are used, such as sucrose, maltose, fructose, lactose and the like.

The formulation of the subject invention may optionally include one of several types of non-ionic surfactants, such as Tween 80. In a preferred embodiment no surfactant is present in the formulation.

Also comprehended by the invention are formulations comprising pharmaceutically effective amounts of protein together with suitable diluents, adjuvants and/or carriers. Other pharmaceutically acceptable excipients well known to those skilled in the art may also form a part of the subject compositions. These include, for example, various bulking agents, additional buffering agents, chelating agents, antioxidants, preservatives, cosolvents, and the like; specific examples of these could include, trimethylamine salts ("Tris buffer"), and EDTA. In one embodiment, more than one type of protein, e.g. IL-3 and G-CSF, are included in the formulation. In another embodiment, no proteins other than the one protein of interest are part of the formulation.

A "pharmaceutically effective amount" of protein residue refers to that amount which provides therapeutic effect in various administration regimens. Such amounts are readily determined by those skilled in the art. The amount of active ingredient will depend upon the severity of the condition being treated, the route of administration, etc. The compositions hereof may be prepared containing amounts of protein of at least about 0.1 mg/ml, upwards of about 5 mg/ml. For G-CSF, preferably from about 0.5 mg/ml to about 2 mg/ml. For use of these compositions in administration to human patients suffering from chronic neutropenia, for example, these compositions may contain from about 0.5 mg/ml to about 4 mg/ml, corresponding to the currently contemplated dosage rate for such treatment. For IL-2, the compositions are prepared containing from about 0.1 to 1.0 mg/ml.

The formulations are prepared in general by combining the components using generally available pharmaceutical combining techniques, known per se. A particular method for preparing a pharmaceutical formulation hereof comprises employing the protein purified according to any standard protein purification scheme.

EXPERIMENTAL

A. Formulation preparation

The pH of G-CSF solution at about 5 mg/ml is adjusted to 3.25±0.1 with 0.5N hydrochloric acid and this solution is diafiltered against water for injection adjusted to pH 3.25 with hydrochloric acid (about 0.56 mM HCl). Diafiltration is continued until the conductivity of the permeate is less than 760 μmhos/cm. This solution is combined with 20% mannitol, and water for injection to obtain a final concentration of 1 mg G-CSF/ml and 5% (w/v) mannitol. If necessary, the pH is adjusted to 3.25 with hydrochloric acid or sodium hydroxide solutions. The solution is then passed through a 0.2 μ filter.

B. Analytical Methods

The analytical methods used are described in the following articles hereby incorporated by reference:
SDS-PAGE: Lammli, U.K. Nature 227, 680-685(1970)
HP-SEC: Watson, E. & Kenney, W. J. Chromatog. 436, 289-298 (1988)

RESULTS

FIG. 1 shows a 15% SDS polyacrylamide gel after reduction of protein thiol groups. The formulations of samples A-H were stored for 2 weeks at 52° C. The G-CSF was formulated at 1 mg/ml with 5% (w/v) mannitol.

| Sample | pH |
|--------|-----|
| A | pH 4.2 |
| B | pH 3.5 |
| C | pH 3.23 |
| D | pH 3.0 |
| E | pH 2.75 |
| F | pH 2.5 |
| G | pH 2.0 |
| H | pH 3.0 + 10 mM NaCl |
| I | pH 3.23 stored at 4° C. |

Figure 2:
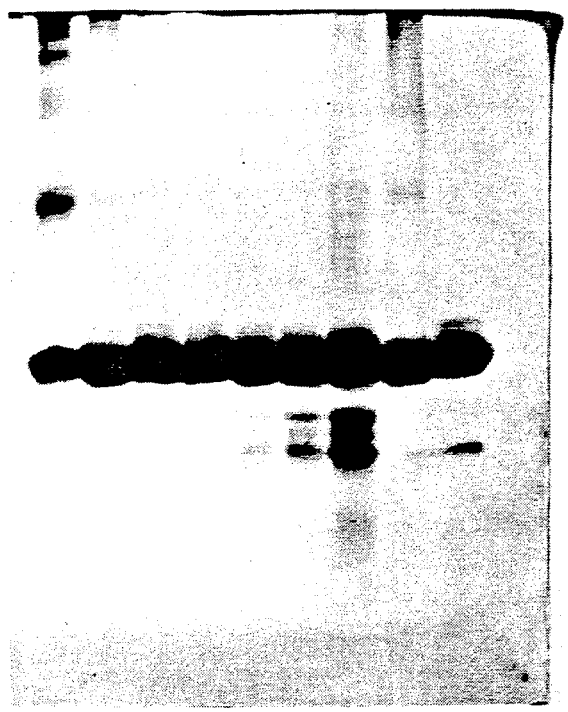
FIG. 2 shows G-CSF prepared at various pH values and run on a 15% non-reducing gel.

FIG. 2 shows a 15% non-reducing SDS polyacrylamide gel. Samples were prepared as in the case of the reducing gel (i.e., 2 weeks at 52° C.).
Note:
(1) the amount of aggregate decreasing with decreasing pH:
A=pH 4.2
B=pH 3.5
C=pH 3.23;

(2) the increasing lower mol. wt. bands due to hydrolysis in E, F, G:
E=pH 2.75
F=pH 2.5
G=pH 2.0;
(3) the higher ionic strength yielding more aggregate:
D=0 NaCl, pH 3.0
H=10 mM NaCl, pH 3.0.

TABLE 1

Percent G-CSF Remaining as Monomer after Incubation for 2 Weeks at 42° C. or 52° C.

| Sample | pH | % monomer[1] 42° C. | 52° C. |
|--------|-----|------|------|
| A | 4.2 | >99 | 39.6 |
| B | 3.5 | >99 | 93.8 |
| C | 3.23 | >99 | 97.6 |
| D | 3.0 | >99 | 98.5 |
| E | 2.75 | >99 | 98.5 |
| F | 2.5 | >99 | 98.3 |
| G | 2.0 | 98.6 | 87.1 |
| H | 3.0 + 10 mM NaCl | >99 | 88.6 |

[1]Starting sample >99% monomer when stored at 4° C.

The results in Table 1 as determined by HP-SEC (Watson, Kenny J. Chromatog. 436, 289-298 (1988)), show that the least amount of aggregate formation was in samples C,D, E & F, which corresponds to a pH range of 3.2-2.50. Further, the presence of salt increased the amount of aggregate (compare D to H). Except for A, & G, little change occurred with incubation at 42°.

Examining the results of FIGS. 1 and 2 and Table 1 together, the most advantageous formulation pH values were those of samples C, D and E, i.e. about pH 2.75-3.23.

Data for IL-2 was substantially the same as that for G-CSF, i.e. the IL-2 was most stable when formulated at a pH of 3-4, and at an conductivity of less than 1000 μmhos/cm, advantageously less than 700 μmhos/cm, and more advantageously less than 500 μmhos/cm.

While the invention has been described in what is considered to be its preferred embodiments, it is not to be limited to the disclosed embodiments, but on the contrary, is intended to cover various modifications and equivalent formulations included within the spirit and scope of the appended claims, which scope is to be accorded the broadest interpretation so as to encompass all such modifications and equivalent formulations.

What is claimed:
1. A stabilized pharmaceutically acceptable formulation consisting essentially of:
   a) a pharmaceutically acceptable amount of G-CSF; and
   b) acid;
   wherein said formulation is at normal temperature, has a pH of 3.0-3.7 and a conductivity of less than 1000 μmhos/cm.
2. A formulation as in claim 1 having a pH of about 3.2-3.3.
3. A formulation as in claim 1 wherein the acid is hydrochloric acid.
4. A formulation as in claim 1 further consisting essentially of a pharmaceutically acceptable tonicity modifier selected from the group consisting of sugars and sugar alcohols.
5. A formulation as in claim 4 wherein the tonicity modifier is mannitol.

6. A formulation as in claim 5 wherein the mannitol is about 5% (w/v) of the formulation.

7. A formulation as in claim 1 which is substantially dimer free.

8. A formulation as in claim 1 further consisting essentially of a nonionic surfactant.

9. A formulation as in claim 1 further consisting essentially of a buffer.

10. A formulation as in claim 1 wherein said hydrophobic protein is G-CSF present at a concentration of 0.5-2 mg/ml, and wherein said formulation has a pH of 3.2-3.3 and a conductivity of less than 200 $\mu$mhos/cm.

11. A method of stabilizing a formulation of G-CSF comprising the step of combining a pharmaceutically acceptable amount of said G-CSF with acid; wherein said formulation is at normal temperature, has a pH of 3.0-3.7, a conductivity of less than 1000 $\mu$mhos/cm, and is pharmaceutically acceptable.

12. A method as in claim 11 wherein said combining also includes adding a pharmaceutically acceptable tonicity modifier selected from the group consisting of sugars and sugar alcohols.

13. A method as in claim 11 wherein said combining step includes adding hydrochloric acid.

14. A method as in claim 11 wherein said formulation has a pH of 3.2-3.3.

15. A method as in claim 11 wherein said combining step does not include adding salt.

16. A method as in claim 12 wherein said tonicity modifier is mannitol.

17. A method as in claim 16 wherein the mannitol is about 5% (w/v) of the formulation.

18. A stabilized pharmaceutically acceptable salt formulation consisting essentially of;
   a) a pharmaceutically acceptable amount of G-CSF; and
   b) acid;
   wherein said formulation is at normal temperature, has an acidic pH and no buffer.

19. A formulation as in claim 18 having a pH of about 2.75-4.

20. A formulation as in claim 18 further consisting essentially of a pharmaceutically acceptable tonicity modifier selected from the group consisting of sugars and sugar alcohols.

21. A formulation as in claim 18 having no surfactant present.

22. A formulation as in claim 18 having a conductivity of less than 1000 $\mu$mhos/cm.

* * * * *